United States Patent [19]

Dockner et al.

[11] 4,298,748

[45] Nov. 3, 1981

[54] PREPARATION OF 2-IMIDAZOLINES

[75] Inventors: Toni Dockner, Meckenheim; Uwe Kempe, Limburgerhof; Herbert Krug, Ludwigshafen; Peter Magnussen, Bad Duerkheim; Werner Praetorius, Darmstadt; Hans J. Szymanski, Schifferstadt, all of Fed. Rep. of Germany

[73] Assignee: BASF Aktiengesellschaft, Fed. Rep. of Germany

[21] Appl. No.: 97,814

[22] Filed: Nov. 27, 1979

[30] Foreign Application Priority Data

Dec. 16, 1978 [DE] Fed. Rep. of Germany ....... 2854428

[51] Int. Cl.$^3$ ................... C07D 233/10; C07D 233/06
[52] U.S. Cl. ..................................... 548/347; 548/355
[58] Field of Search ................................ 548/347, 355

[56] References Cited

U.S. PATENT DOCUMENTS

| | | | |
|---|---|---|---|
| 2,505,247 | 4/1950 | Isler et al. ........................... | 548/347 |
| 3,210,371 | 10/1965 | Sawa et al. .......................... | 548/347 |
| 3,360,506 | 12/1967 | De Benneville et al. ........... | 548/347 |
| 3,629,278 | 12/1971 | Bachman ............................. | 548/347 |
| 3,903,104 | 9/1975 | Cognaw ............................... | 548/347 |
| 4,189,589 | 2/1980 | Meyer et al. ........................ | 548/347 |

FOREIGN PATENT DOCUMENTS

| | | |
|---|---|---|
| 2512513 | 7/1976 | Fed. Rep. of Germany . |
| 2615886 | 10/1977 | Fed. Rep. of Germany . |
| 49-24965 | 11/1974 | Japan . |

OTHER PUBLICATIONS

Oxley et al., J. Chem. Soc. (1947), pp. 497–505.
Waldman et al., Chem. Ber. 74 (1941), pp. 1763–1766.
Riebsomer, J. Amer. Chem. Soc. 70 (1948), pp. 1629–1632.
Ullmanns Encyklopädie der Technischen Chemie, vol. 13, pp. 331–338, and vol. 1, p. 916.

*Primary Examiner*—Henry R. Jiles
*Assistant Examiner*—Jane T. Fan
*Attorney, Agent, or Firm*—Keil & Witherspoon

[57] ABSTRACT

A novel process for the preparation of 2-imidazolines by reacting 1,2-diamines with nitriles or carbonyl compounds in the gas phase at from 200° to 450° C. in the presence of an oxide or phosphate of a metal of group 3 or 4 of the periodic table and/or in the presence of silicon dioxide.

The 2-imidazolines obtainable by the process of the invention are valuable starting materials for the preparation of dyes, crop protection agents and drugs.

14 Claims, No Drawings

PREPARATION OF 2-IMIDAZOLINES

The present invention relates to a novel process for the preparation of 2-imidazolines by reacting 1,2-diamines with nitriles or carbonyl compounds in the gas phase at from 200° to 450° C. in the presence of an oxide or phosphate of a metal of group 3 or 4 of the periodic table and/or in the presence of silicon dioxide.

J. Chem. Soc. (1947), 497–505 discloses that salts of ethylenediamine, when reacted with nitriles at from 200° to 270° C., give 2-substituted 2-imidazolines. The yields of end products are unsatisfactory. Japanese Published Pat. No. 24,965/1964 states that sulfur in lump form catalyzes the condensation of 1,2-diamines with nitriles. This publication points out, and demonstrates for certain catalysts, that with other sulfur compounds and modifications than sulfur in lump form the yield is lower or there is no reaction at all. Thus, hydrogen sulfide gives only 16.1 percent yield and in the case of octylmercaptan there is no reaction at all. Inorganic sulfides or polysulfides are not mentioned. The process is unsatisfactory in respect of simplicity of operation and of yield of end product.

Chem. Ber. 74 (1941), 1,763–1,766 discloses that lauric acid can be reacted with an excess of ethylenediamine hydrochloric and ethylenediamine hydrochloride at from 280° to 290° C. to give undecyl-imidazoline hydrochloride. It states that if instead of the hydrochloride only the free base is used, the reaction gives only small amounts of imidazoline, in addition to dark decomposition products and a large amount of dilauroyl-ethylenediamine. The isolation of the end product from the reaction mixtures requires several purification stages, for example dissolving the mixture in water, precipitating with sodium hydroxide solution, extracting by shaking with ether, washing the ether extracts with sodium chloride solution and evaporating off the ether.

A publication in J. Amer. Chem. Soc. 70 (1948), 1,629–1,632 discloses that the reaction can also be carried out with the free base in the absence of hydrochloric acid, at from 180° to 220° C.; as shown by the description and all the Examples, the reaction is intended to be carried out with a molar ratio of the reactants of 1:1, and in the presence of benzene in the reaction mixture. During the reaction, an azeotropic mixture of benzene and water is distilled off. In spite of this special procedure, substantial amounts of a high-boiling by-product are always found alongside the imidazoline. The publication describes, and shows with Examples, that the yield of this by-product increases with the number of carbon atoms in the alkanecarboxylic acid molecule; for example, reactions with acetic acid give a 32.7 percent yield, and those with myristic a 92.5 percent yield, of high-boiling by-product. In the case of stearic acid, only the by-product is obtained, the yield being virtually quantitative. The yields of imidazoline are 26.6 percent in the case of acetic acid, 13.3 percent in the case of formic acid, 12.9 percent in the case of propionic acid and 15.4 percent in the case of caproic acid. The yields for longer-chain carboxylic acids are not stated. The recovery of a part of the imidazoline from the by-product is only possible by laborious methods, for example by treatment with aqueous sodium hydroxide solution, extraction with ether, drying the ether extract over solid potassium hydroxide, evaporation of the ether and fractional distillation.

German laid-open application DOS No. 2,512,513 discloses a process for the preparation of 2-imidazolines by reaction of 1,2-diamines with nitriles in the presence of polysulfides as catalysts. Disadvantages of the process are the formation of sulfur-containing by-products which are difficult to separate off and which interfere with the catalyst during the subsequent dehydrogenation reaction.

German laid-open application DOS No. 2,615,886 describes a process for the preparation of 2-imidazolines by reacting alkanecarboxylic acids with an excess of 1,2-diamines at below 160° C., with removal of water. Disadvantages of the process are the low space-time yields, and the fact that at least 2 moles of diamine are required per mole of alkanecarboxylic acid.

We have found that a 2-imidazoline of the formula

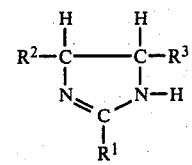

where $R^1$, $R^2$ and $R^3$ may be identical or different and each is an aliphatic, cycloaliphatic, araliphatic or aromatic radical, and $R^2$ and $R^3$ may also each be hydrogen, is obtained in an advantageous manner by catalytic reaction of a 1,2-diamine with a carbonyl compound or a nitrile, if a 1,2-diamine of the formula

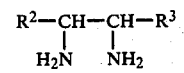

where $R^2$ and $R^3$ have the above meanings, is reacted (a) with a nitrile of the formula

or (b) with a carbonyl compound of the formula

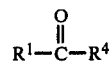

where $R^1$ has the above meaning and $R^4$ is $-OR^2$, $-NH^2$ or

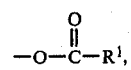

$R^1$ and $R^2$ having the above meanings, in the gas phase at from 200° to 450° C. in the presence of an oxide or phosphate of a metal of group 3 or 4 of the periodic table and/or in the presence of silicon dioxide.

Further, we have found that the reaction can advantageously be carried out in the additional presence of phosphoric acid and/or a phosphoric acid ester.

When using ethylenediamine and acetonitrile, or 1,2-diaminopropane and isobutyric acid, the reaction can be represented by the following equations respectively:

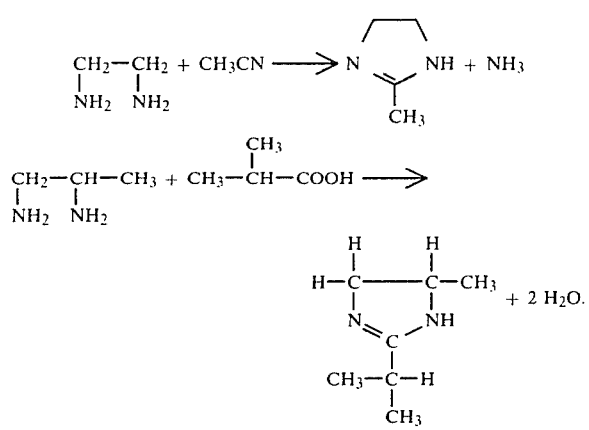

Compared to the first of the conventional processes mentioned, the process according to the invention gives 2-imidazolines more simply and more economically, in better yield and greater purity. Though the reaction is carried out with the free base, no substantial amounts of decomposition products, complex compounds or high-boiling by-products are observed. Involved multi-stage purification operations are avoided.

Compared to the processes described in German laid-open application DOS Nos. 2,512,513 and 2,615,886, the process according to the invention surprisingly gives 2-imidazolines more simply and more economically, in some cases in better yield and greater purity, and with better space-time yield. Compared to German laid-open application DOS No. 2,615,886, the amounts of diamine required are less. Sulfur-containing catalysts are not used and hence the process causes less pollution of the environment. Compared to the polysulfide catalyst described in German laid-open application DOS No. 2,512,513, the catalyst used according to the invention has a longer life and gives the end product in constant high yield even when the plant has been run for more than 3,000 hours. Even after regeneration, the life of the catalyst according to the invention is longer than that of prior art catalysts; for example, even after operating for more than 1,000 hours and end product is still obtained in high yield. The formation of cracking products on the catalyst, which would reduce or inhibit the active centers of the catalyst, is substantially avoided. The economics and reliability of operation of the preparation of 2-imidazolines are decisively improved by the novel process. These advantageous results are surprising in view of the prior art.

The starting materials are reacted with one another in stoichiometric amounts or using an excess of one or the other, preferably in a ratio of from 1 to 2, especially from 1 to 1.2, moles of starting material II per mole of starting material III or IV. Preferred starting materials II, III and IV and, accordingly, preferred end products I are those where $R^1$, $R^2$ and $R^3$, which may be identical or different, are each alkyl of 1 to 18 carbon atoms, especially of 1 to 7 carbon atoms, cyclohexyl, cyclopentyl, aralkyl of 7 to 12 carbon atoms, naphthyl or phenyl, $R^2$ and $R^3$ may in addition also each be hydrogen, and $R^4$ is $-OR^2$, $-NH_2$ or $$-O-\underset{\underset{O}{\|}}{C}-R^1,$$

with $R^1$ and $R^2$ having the above preferred meanings. If an ester or acid is used as the carbonyl compound IV, the radicals $R^2$ in the starting material II and IV may be identical or different. Mixed acid anhydrides may also be used as starting materials IV. The above radicals may in addition be substituted by groups which are inert under the reaction conditions, for example alkyl or alkoxy, each of 1 to 4 carbon atoms.

Examples of suitable starting materials II are ethylenediamine, 1,2-propylenediamine, 1,2butylenediamine, 1,2-pentylenediamine, 1,2-n-hexylenediamine, 1,2-n-heptylenediamine, 1,2-n-octylenediamine, 1,2-n-nonylenediamine and 1,2-n-decylenediamine; corresponding alkanes with 2 adjacent amino groups on two other carbon atoms in the molecule; 2-cyclohexyl-, 2-cyclopentyl-, 2-benzyl-, 2-phenyl-, 2-o-methoxyphenyl-, 2-m-methoxyphenyl-, 2-p-methoxyphenyl-, 2-2',5'-dimethylphenyl-, 2-2',6'-dimethylphenyl-, 2-2',4'-dimethylphenyl-, 2-2',3'-dimethylphenyl-, 2-o-toluyl-, 2-m-toluyl-, 2-p-toluyl-, 2-o-ethylphenyl-, 2-m-ethylphenyl- and 2-p-ethylphenyl-1,2-ethylenedimine; 1,2-dicyclohexyl-, 1,2-dicyclopentyl-, 1,2-dibenzyl-, 1,2-diphenyl-, 1,2-di-o-methoxyphenyl-, 1,2-di-m-methoxyphenyl-, 1,2-di-p-methoxyphenyl-, 1,2-di-2',5'-dimethylphenyl, 1,2-di-2',6'-dimethylphenyl-, 1,2-di-2',4'-dimethylphenyl, 1,2-di-2',3'-dimethylphenyl-, 1,2-di-o-toluyl-, 1,2-di-m-toluyl- and 1,2-di-p-toluyl-1,2-ethylenediamine.

Examples of suitable starting materials III are stearonitrile, palmitonitrile, acetonitrile, propionitrile, butyronitrile, isobutyronitrile, pentanecarboxylic acid nitrile, 2-ethylhexanecarboxylic acid nitrile, caprylonitrile, trimethylacetonitrile, isovaleronitrile, valeronitrile, 2,3-dimethylbenzonitrile, 2,4-dimethylbenzonitrle, 2,5-dimethylbenzonitrile, 2,6-dimethylbenzonitrile, benzonitrile, phenylpropionitrile, cyclopentanecarboxylic acid nitrile, cyclohexanecarboxylic acid nitrile, phenylacetonitrile, o-toluic acid nitrile, m-toluic acid nitrile and p-toluic acid nitrile.

Examples of suitable starting materials IV are acrylic acid, formic acid, acetic acid, propionic acid, butyric acid, isobutyric acid, tetracosanoic acid, hexacosanoic acid, linoleic acid, linolenic acid, ricinoleic acid, erucic acid, myristic acid, arachidic acid, behenic acid, oleic acid, elaidic acid, caproic acid, enanthic acid, pelargonic acid, capric acid, 3,5,5-trimethylhexanoic acid, undecanoic acid, lauric acid, palmitic acid, stearic acid, 2-ethylhexanecarboxylic acid, α-ethylbutyric acid, methacrylic acid, crotonic acid, isocrotonic acid, tiglic acid, sorbic acid, undecylenic acid, 2-methylbutanoic acid, trimethylacetic acid, valeric acid, isovaleric acid, isocaproic acid, nonanoic acid, tridecanoic acid, pentadecanoic acid and heptadecanoic acid, and corresponding mixtures, such as the mixtures obtained from the preparation of natural or synthetic fatty acids. Such mixtures are obtained, for example, by the splitting of fats, by paraffin oxidation or by oxo reaction from olefins, carbon monoxide and water. Other suitable compounds are the acid amides and acid anhydrides corresponding to the above acids, and the esters of the above acids with methanol, isopropanol, ethanol, undecanol, dodecanol, n-propanol, tert.-butanol, nonanol, sec.-butanol, n-hexanol, n-butanol, iso-butanol, 2-ethylhexanol, cyclohexanol, benzyl alcohol, cyclopentanol, cycloheptanol, phenylethyl alcohol, n-pentanol, phenol, n-heptanol, n-octanol and n-decanol.

The reaction is conveniently carried out at from 230° to 420° C., advantageously from 260° to 400° C., preferably from 300° to 380° C., under atmospheric or superatmospheric pressure (advantageously from 1 to 10 bar), continuously or batchwise. The temperature and pressure conditions are selected so that the reaction takes place in the gas phase. Carrier gases which are inert under the reaction conditions, eg. nitrogen, may advantageously be present, suitable amounts being from 20 to 80 percent by weight, based on the amount by weight of starting material II.

The reaction is carried out in the presence of a catalyst consisting of an oxide and/or phosphate of a metal of group 3 and/or group 4 of the periodic table and/or of silicon dioxide. Preferred metal compounds of this type are based on the metals of groups IIIa, IVa and IVb of the periodic table (the group designation being in accordance with D'Ans-Lax, Taschenbuch für Chemiker and Physiker (Springer, Berlin, 1967), volume 1, page 63; Clark, the Encyclopedia of Chemistry, 2nd edition (Reinhold Pub. Corp., N.Y., 1966), page 790), especially calcium, aluminum, titanium or thorium, γ-Aluminum oxide is particularly preferred. The said compounds may be used individually or as mixtures with one another. In general, if the process is carried out batchwise the catalyst is used in an amount of from 1 to 50, preferably from 2 to 20, especially from 5 to 10, percent by weight based on starting material II. If the reaction is carried out continuously, from 5 to 15 moles of starting material II are as a rule employed per hour per liter of catalyst.

Before use, the metal oxides and metal phosphates used as catalysts can be modified in respect of structure or surface condition by physical or chemical treatment, for example by heating, treatment with steam or impregnation with acids, eg. phosphoric acid or boric acid, or with salt solutions, eg. of nitrates, formates or oxalates of the above metals. The catalyst can also be applied to a carrier, for example quartz powder, a ceramic or pumice, by impregnation or precipitation, after which it may or may not be converted to its final oxide form by heat treatment or decomposition. Catalysts which contain both the metal compound and silicon dioxide advantageously comprise from 1 to 30, especially from 5 to 15 percent by weight of metal oxide and/or metal phosphate, based on silicon dioxide. The carriers may additionally contain compounds of other elements, which do not substantially influence the reaction, for example sodium compounds.

The silicon dioxide is in general used in the form of silica compounds. These are advantageously silicates, for example sodium aluminum silicate, calcium aluminum silicate, bleaching earths, fuller's earth, clays, kaolin, allophanes, zeolites, montmorillonite, pumice, Florida earth, asbestos, mullite and bentonite, or silicic acid, silica gel, kieselguhr, silica aerogel, silica xerogel, polysilicic acids, Aerosil, quartz, coesite, cristobalite, and tridymite. In the present specification, the silica compound is calculated as $SiO_2$, regardless of its actual structure and composition. Frequently, the silica compound advantageously serves as part of the active composition and at the same time as a carrier for the other part of the active composition, for example the metal compound and/or especially the phosphoric acid. A catalyst may advantageously be prepared as follows: commercial sodium waterglass is converted, by addition of sulfuric acid, into a water-rich silica hydrogel via the intermediate stage of a silica sol, and the hydrogel is eluted with 20% strength by weight aqueous ammonia and thus freed from salts. After this treatment, the hydrogel is treated with phosphoric acid, advantageously in the presence of oxalic acid, for example of from 5 to 15 percent by weight of oxalic acid based on silicon dioxide, in a mill or some other apparatus which generates shearing forces, during which treatment peptization occurs. The aqueous phase obtained is spray-dried in a stream of gas at from 200° to 400° C., for example in a stream of flue gas, whereupon the catalyst is obtained in the form of a granular powder. This method of preparation of the catalyst is particularly advantageous if the catalyst is used in a fluidized bed. The phosphoric acid is advantageously applied to the silica compound in the form of an aqueous solution containing from 50 to 90, preferably from 60 to 80, percent by weight of phosphorus pentoxide.

The shape and size of the catalyst particles are not a critical factor in the reaction. A particle size of from 0.03 to 10 millimeters, especially from 0.1 to 4 millimeters, and a specific total surface area of the catalyst of from 50 to 450 square meters per gram are preferred. The specific total surface area means the total inner and outer surface area per gram of catalyst. The conventional methods may be used to determine the specific total surface area of the catalyst, for example the BET method (Ullmanns Encykolpädie der technischen Chemie, Volume 9, page 266). Where a fluidized bed process is used, particle sizes of from 0.06 to 0.5 millimeters and a specific total surface area of from 250 to 500 m$^2$/g are advantageous. In general, the pores of the catalyst should have a radius of from 15 to 100, advantageously from 30 to 80, Å. The catalyst may be in any desired form, for example amorphous, in the form of extrudates, spherical or granular. Regarding the preparation of the catalysts, reference may be made to Houben-Weyl, Methoden der Organischen Chemie, Volume 4/2, pages 142 et seq. and Ullmanns Encyklopädie der technischen Chemie, Volume 9, pages 271 et seq. and Volume 15, pages 712 et seq.

Additional catalysts used are advantageously phosphoric acid and/or one or more phosphoric acid esters; advantageous amounts are from 0.01 to 1, especially from 0.01 to 0.1, percent by weight based on starting material II. In relation to the other constituents of the catalyst, advantageous amounts are from 1 to 30, especially from 5 to 15, percent by weight of phosphoric acid, based on the weight of metal oxide and/or silicon dioxide, or from 1 to 25, especially from 2 to 10, percent by weight of phosphoric acid, based on the weight of metal phosphate. The phosphoric acid may be entirely or partially in the form of phosphorus pentoxide, orthophosphoric acid, metaphosphoric acid, pyrophosphoric acid or polyphosphoric acid, for example containing from 72 to 88 percent by weight of $P_2O_5$, and is, in the present specification, calculated as $H_3PO_4$ regardless of the actual structure of the phosphoric acid or of the phosphorus pentoxide. Where esters are used, these may be monoesters, diesters or preferably triesters. Examples of suitable esters are cycloaliphatic, araliphatic, aromatic and especially aliphatic esters of phosphoric acid, especially esters of up to 12 carbon atoms per organic group, e.g. triethyl, tri-n-butyl, trimethyl, O,O-diethyl-O-phenyl, O-ethyl-O, O-diphenyl, tricyclohexyl, tribenzyl, O,O-dimethyl-O-ethyl, tris-2-ethylhexyl, tris-β-chloroethyl, tris-β-butoxyethyl, tris-β-methoxyethyl, di-(2-ethylhexyl), dioctyl, octadecyl, tricresyl, O,O-diphenyl-O-cresyl, trixylenyl, tris-(p-tert.-butylphenyl), O,O-diphenyl-O-bisphenyl and O,O-diphenyl-O-methyl phosphate. The additional catalyst may be combined with the metal oxide/metal phosphate catalyst in the conventional manner, for example by impregnating, spraying, mixing or conjoint milling. More advantageously, the additional catalyst is added to the starting material II or the initial mixture of starting materials or, where appropriate, to the carrier gas, before starting the reaction.

The reaction may be carried out as follows: a mixture of the starting materials II and III is passed over the catalyst, heated to the reaction temperature, in a tubular reactor or fluidized bed reactor. Where appropriate, gases which are inert under the reaction conditions, for example nitrogen, may be fed over the catalyst in addition to the reaction mixture. An advantageous residence time is from 2 to 40, especially from 3 to 20, seconds in the reaction chamber. The end product is isolated from the reaction mixture leaving the reactor by conventional methods, for example by fractional distillation. However, it is also possible to take samples of the reaction mixture, ascertain the conversion by analytical, for example gas-chromatographic, determination of the ratio of end product I to starting material II therein and process the reaction mixture further directly, for example to the corresponding imidazoles, without isolating the imidazoline end product.

In a preferred embodiment of the process, the starting materials are reacted in a fluidized bed at the reaction temperature. The catalyst, or supported catalyst, can advantageously be kept in the form of a fluidized bed, using, as the fluidizing gas, an inert gas, a mixture of starting materials II and III or IV and inert gas, or the mixture of starting materials alone, under atmospheric, reduced or superatmospheric pressure. Correspondingly, the total amount, or a part, of the starting materials may be introduced into the fluidized bed reactor separately from the fluidization gas. The starting materials may also be kept liquid in a heated stock vessel and be fed from there to a vaporizer upstream of the fluidized bed reactor. It is advantageous at the same time to pass a slight stream of nitrogen, advantageously from 5,000 to 50,000 parts by volume of nitrogen per hour, through the vaporizer. The vaporized starting materials are passed, together with the stream of nitrogen, through the catalyst bed. The concentration of the starting material II in the inert gas is advantageously from 0.1 to 50 percent by volume. The process according to the invention can be carried out in a simple or compartmented, open or closed fluidized bed system. with or without dust circulation, Regarding the reactors, the method of operation, the various possible embodiments and the reaction conditions for fluidized bed processes, reference may be made to Ullmanns Encyklopädie der technischen Chemie, Volume 1, pages 916 et seq. The reaction mixture is worked up as described above.

The 2-imidazolines I obtainable by the process of the invention are valuable starting materials for the preparation of dyes, crop protection agents and drugs. 2-Imidazolines I are employed as catalysts for polymerization reactions and aldol condensations. On dehydrogenation over aluminum/zinc oxide catalysts they give the corresponding imidazoles. Regarding their use, reference may be made to the above publications and to Ullmanns Encyklopädie der technischen Chemie, Volume 13, pages 331 and 338.

In the Examples which follow, parts are by weight and bear the same relations to parts by volume as that of the kilogram to the liter.

EXAMPLE 1

Per hour, 132 parts of 1,2-diaminoethane are mixed with 120 parts of acetic acid at 38° C., with stirring and cooling. The ethylenediamine monoacetate formed solidifies below 35° C. to a crystalline mass whilst above this temperature it remains liquid. 252 parts per hour of this mixture are metered from a stock vessel into a horizontal quartz vaporizer heated to 300° C., and the vapor, together with 5,000 parts by volume of nitrogen per hour, is passed through the fluidized bed reactor heated to 300° C. The reactor is a vertical electrically heated quartz tube fitted onto the vaporizer and closed at the bottom by a quartz frit sealed into the tube. The tube is half filled with 200 parts of a catalyst containing 5 percent by weight of $H_3PO_4$ and 95 percent by weight of γ-aluminum oxide. The residence time in the catalyst zone, when fluidized, is 3.5 seconds, and the height of the catalyst zone, when fluidized, is 80 mm. The vapors leaving the reactor are condensed and subjected to fractional distillation. Per hour, 159.6 parts (95% of theory, based on acetic acid) of 2-methylimidazoline, of boiling point 73° C./2.66 mbar, and melting point 103° C., are obtained. The conversion is 88.5 percent, based on diamine II. The yield remained constant even after 300 hours' operation.

EXAMPLE 2

The procedure described in Example 1 is followed, except that only γ-$Al_2O_3$, without $H_3PO_4$, is employed as the catalyst. 161 parts per hour (96% of theory) of 2-methylimidazoline of boiling point 73° C./2.66 mbar are obtained.

EXAMPLE 3

The procedure described in Example 1 is followed, except that the catalyst employed contains 95 percent by weight of $SiO_2$ and 5 percent by weight of $H_3PO_4$. 159.6 parts per hour (95% of theory) of 2-methylimidazoline of boiling point 73° C./2.66 mbar are obtained.

EXAMPLE 4

The procedure described in Example 1 is followed, except that a pure $SiO_2$ catalyst without $H_3PO_4$ is employed. 159.6 parts per hour (95% of theory) of 2-methylimidazoline of boiling point 73° C./2.66 mbar are obtained.

EXAMPLE 5

176 parts of n-butyric acid and 132 parts of ethylenediamine are introduced, with 40,000 parts by volume of $N_2$, into the quartz vaporizer and are vaporized at 300° C. and passed, at the same temperature, over 200 parts by weight of the catalyst described in Example 1. 215 parts of 2-n-propylimidazoline (96% of theory, based on n-butyric acid employed), of boiling point 87° C./5.32 mbar are obtained.

EXAMPLE 6

The procedure described in Example 5 is followed except that 288 parts of n-octanoic acid and 132 parts of ethylenediamine are employed. 319 parts of 2-n-heptylimidazoline (95% of theory, based on octanoic acid employed) of boiling point 133° C./5.32 mbar are obtained.

EXAMPLE 7

The procedure described in Example 5 is followed except that 176 parts of isobutyric acid and 162.8 parts of 1,2-diaminopropane are employed. 201 parts of 2-isopropyl-4(5)-methylimidazoline (80% of theory, based on isobutyric acid employed) of boiling point 105°–106° C./32 mbar are obtained.

EXAMPLE 8

The procedure described in Example 5 is followed except that 272 parts of methyl benzoate and 132 parts of ethylenediamine are employed. 277 parts of 2-phenylimidazoline (95% of theory, based on methyl benzoate employed) of boiling point 295° C./1,013 mbar are obtained.

EXAMPLE 9

The procedure described in Example 5 is followed except that 300 parts of methyl phenylacetate and 132 parts of ethylenediamine are employed. 288 parts of benzylimidazoline (90% of theory, based on methyl phenylacetate employed) of boiling point 155°–161° C./3 mbar are obtained.

EXAMPLE 10

The procedure described in Example 5 is followed except that 82 parts of acetonitrile and 132 parts of ethylenediamine are employed. 149 parts (91% of theory) of 2-methylimidazoline, of boiling point 73° C./2.66 mbar, are obtained.

EXAMPLE 11

The procedure described in Example 5 is followed except that 206 parts of benzonitrile and 132 parts of ethylenediamine are employed. 273.6 parts (95% of theory) of 2-phenylimidazoline, of boiling point 295° C./1,013 mbar, are obtained.

EXAMPLE 12

The procedure described in Example 5 is followed except that 118 parts of acetamide and 132 parts of ethylenediamine are employed. 159.6 parts (95% of theory) of 2-methylimidazoline, of boiling point 73° C./2.66 mbar, are obtained.

We claim:

1. A process for the preparation of a 2-imidazoline of the formula

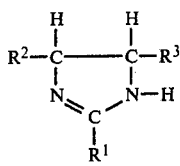   I where $R^1$, $R^2$ and $R^3$ may be identical or different and each is an aliphatic, cycloaliphatic, araliphatic or aromatic radical, and $R^2$ and $R^3$ may also each be hydrogen, by catalytic reaction of a 1,2-diamine with a carbonyl compound or a nitrile, wherein a 1,2-diamine of the formula

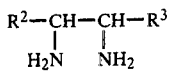   II where $R^2$ and $R^3$ have the above meanings, is reacted
(a) with a nitrile of the formula

   III or
(b) with a carbonyl compound of the formula

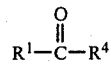   IV where $R^1$ has the above meaning and $R^4$ is $-OR^2$, $-NH^2$ or

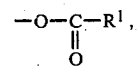

$R^1$ and $R^2$ having the above meanings, in the gas phase at from 200° to 450° C. in the presence of silicon dioxide.

2. The process of claim 1, wherein the reaction is carried out in the additional presence of phosphoric acid or a phosphoric acid ester.

3. The process of claim 1, wherein the reaction is carried out with from 1 to 2 moles of starting material II per mole of starting material III or IV.

4. The process of claim 1, wherein the reaction is carried out at from 230° to 420° C.

5. The process of claim 1, wherein the reaction is carried out at from 260° to 400° C.

6. The process of claim 1, wherein the reaction is carried out at from 300° to 380° C.

7. The process of claim 1, wherein the reaction is carried out using a carrier gas which is inert under the reaction conditions.

8. The process of claim 1, wherein the reaction is carried out using from 1 to 50 percent by weight of catalyst, based on starting material II, or, if the process is carried out continuously, with from 5 to 15 moles of starting material II per hour per liter of catalyst.

9. The process of claim 1, wherein the reaction is carried out with a catalyst which contains from 1 to 30 percent by weight, based on silicon dioxide, of the metal oxide or metal phosphate.

10. The process of claim 1, wherein the reaction is carried out with catalyst particles which have a size of from 0.03 to 10 millimeters and a specific total surface area of from 50 to 450 square meters per gram or, when using the fluidized bed process, a particle size of from 0.06 to 0.5 millimeters and a specific total surface area of from 250 to 500 m²/g.

11. A process as claimed in claim 1, wherein the reaction is carried out with a catalyst having a pore radius of from 15 to 100 Å.

12. A process as claimed in claim 2, wherein the reaction is carried out with from 0.01 to 1 percent by weight, based on starting material II, of phosphoric acid or one or more phosphoric acid esters.

13. A process as claimed in claim 1, wherein the reaction is carried out with from 1 to 30 percent by weight of phosphoric acid, based on weight of metal oxide or silicon dioxide, or with from 1 to 25 percent by weight of phosphoric acid, based on weight of metal phosphate.

14. The process of claim 1 or 2, wherein the reaction is carried out in the further presence of an oxide or phosphate of calcium or a metal of group 3 or 4 of the periodic table.

* * * * *

UNITED STATES PATENT AND TRADEMARK OFFICE
CERTIFICATE OF CORRECTION

PATENT NO. : 4,298,748
DATED : November 3, 1981
INVENTOR(S) : T. Dockner, U. Kempe, H. Krug, P. Magnussen, W. Praetorius and H.J. Szymanski It is certified that error appears in the above—identified patent and that said Letters Patent is hereby corrected as shown below:

IN THE CLAIMS:

In line 1 of claims 9, 10 and 13, the claims should be corrected to depend on claim 14 rather than on claim 1. Also the claims should be renumbered as necessary.

In line 3 of Claim 11, "A" should be -- R --.

Signed and Sealed this

Eighth Day of June 1982

[SEAL]

Attest:

Attesting Officer

GERALD J. MOSSINGHOFF
Commissioner of Patents and Trademarks